United States Patent [19]
Lee et al.

[11] Patent Number: 5,386,055
[45] Date of Patent: Jan. 31, 1995

[54] DEPOLYMERIZATION PROCESS

[75] Inventors: Sunggyu Lee, Akron; Mehmet A. Gencer, Brecksville; Kathy L. Fullerton, Cuyahoga Falls; Fouad O. Azzam, Canton, all of Ohio

[73] Assignee: The University of Akron, Akron, Ohio

[21] Appl. No.: 105,885

[22] Filed: Aug. 11, 1993

[51] Int. Cl.⁶ .............................................. C07C 1/00
[52] U.S. Cl. ................... 562/512.2; 562/542; 48/127.5; 48/197 R; 210/180; 210/181; 210/761; 252/183.11; 570/101; 585/6; 585/801; 585/241
[58] Field of Search .................... 562/512.2, 542; 570/101; 585/6, 241, 801; 48/127.5, 197 R; 210/180, 181, 761; 252/183.11; 423/488; 568/806; 540/538

[56] References Cited

U.S. PATENT DOCUMENTS

| | | | |
|---|---|---|---|
| 4,031,192 | 6/1977 | Hafeli | 423/488 |
| 4,543,190 | 9/1985 | Modell | 210/721 |
| 5,136,111 | 8/1992 | Chum et al. | 568/806 |
| 5,216,149 | 6/1993 | Evans et al. | 540/538 |

OTHER PUBLICATIONS

"Catalytic Selective Oxidation"–ACS Symposium Series 523, S. Ted Oyama, Editor, and Joe W. Hightower, Editor, Aug. 23–28, 1992.

*Primary Examiner*—Arthur C. Prescott
*Attorney, Agent, or Firm*—Hudak & Shunk Co.

[57] ABSTRACT

A process for depolymerizing polymers by selective, partial oxidation at supercritical or near supercritical conditions for water and wherein supercritical water or water near supercritical conditions is used as a solvent and reforming agent, is used to produce relatively high yields of the monomers originally used to produce the polymers. The invention provides an environmentally friendly process for recycling polymeric waste materials to generate valuable polymer feedstock in a closed oxidation process which is free of hazardous stack emissions. The polymers which can be recycled in accordance with the process can include typical amounts of conventional additive and other impurities without significantly affecting the overall conversion.

29 Claims, 7 Drawing Sheets

DEPOLYMERIZATION PROCESS

FIELD OF THE INVENTION

The invention relates generally to a method for depolymerizing a polymeric material to recover valuable low molecular weight components, and more particularly the invention relates to an oxidative precision depolymerization process for converting polymeric materials into monomers and oligomers thereof which can be polymerized to reform a pure or virgin polymer.

BACKGROUND

It is well known that polymers, like other organically based waste materials, can generally be combusted to produce carbon dioxide, water and other products along with useable energy. Another oxidation process which can be utilized is wet air oxidation wherein the feed and oxidizing agent are pressurized to reaction conditions of from about 1500 to 2500 psig, heated to operating temperature and fed to a reactor for residence times of 0.5 to 1 hour. Catalytic oxidation processes can also be used to convert polymers to carbon dioxide, water and other products depending on the composition of the polymer. All of the known reaction techniques for recycling polymers, however, are generally directed toward achieving or nearly achieving complete oxidation of the polymer in order to recover the maximum amount of thermal energy. Accordingly, none of the known methods for oxidizing polymers has been successfully utilized for achieving selective oxidation to recover high yields of monomers and oligomers thereof which can be used to repolymerize the pure polymer.

The recovery of monomers from polymeric waste material is highly desirable because other means of recycling polymers such as melting thermoplastics and reshaping them into usable articles has only limited applications owing to the tendency of such polymeric materials to undergo progressive contamination and degradation leading to lower quality materials which are unsuitable for many applications.

SUMMARY OF THE INVENTION

In accordance with the process of the invention, it has been discovered that various polymers can be depolymerized when selectively partially oxidized in a supercritical water mixture or in a water mixture near supercritical conditions. Specifically, it has been found that addition type polymers, i.e. chain polymerization, particularly those with strong electron withdrawing groups, can be oxidatively depolymerized to produce high yields of the monomer from which the polymer was originally polymerized along with progressively diminishing quantities of dimers, trimers and higher molecular weight oligomers of the monomer. Other polymers including condensation type polymers and addition type polymers which are free of strong electron withdrawing groups can also be depolymerized using the process of the invention to produce useful products such as, for example, combustible fuels; however, monomer yields are generally lower.

Depolymerization in accordance with the process of the invention is achieved by forming a homogeneous or pseudohomogeneous mixture of a suitable polymer including both addition and condensation type polymers, water at supercritical conditions, and an amount of an oxidant which is effective to cause selective oxidation of the polymer. The supercritical water is used as both a solvent and reforming agent for the polymer. At supercritical water conditions, oxygen and nitrogen are completely miscible with water in all proportions creating a single fluid phase in contact with the polymer. The polymer is preferably comminuted to form small particles which are dispersed in the supercritical fluid. The polymer swells and dissolves or at least becomes intimately dispersed within the fluid medium creating a homogeneous or at least a pseudohomogeneous mixture. The resulting mixture behaves as a single fluid phase eliminating or substantially reducing the need for complicated apparatus and mechanical mixing equipment generally required for handling heterogeneous reaction mixtures. In addition, the single homogeneous or pseudohomogeneous mixture reduces mass transfer resistances to levels substantially below those of heterogeneous reaction systems, thus facilitating rapid and uniform reactions and thereby eliminating or at least substantially reducing the need for oxidation catalysts. The single phase system also allows for reduced residence times and/or reduced size for the reactor and associated equipment as compared with heterogeneous reaction systems. The high solvent power of the supercritical water also keeps organic intermediates well solvated and dispersed thereby eliminating char-forming reactions.

The process can be utilized for recycling pure polymers such as to reduce waste and optimize product yield at polymer manufacturing facilities, or to recycle polymers containing normal amounts of conventional additives such as plasticizers, filler, pigments, etc.

To prevent undesirable reactions such as pyrolysis and charring, the reactants are preferably mixed so that the polymer is rapidly brought to a sufficiently high temperature so that when the oxidant is brought into contact with the polymer and water, the water is at supercritical conditions. That is to say, the temperature of the polymer is preferably raised from near ambient conditions to the critical temperature of water as quickly as possible, and the amount of time wherein the oxygen is in contact with the polymer at conditions below the critical temperature and pressure of water is preferably kept to a minimum. Preferably, the polymer is rapidly brought to a temperature above the critical temperature of water (374° C.) by contacting the polymer directly with supercritical water and thus raising the temperature of the mixture substantially instantaneously and minimizing or substantially eliminating char formation. The oxidant is preferably mixed with the polymer-supercritical water mixture at or just before the inlet of the reaction vessel. Oxidation catalysts such as common metal oxides or supported metal catalyst which provide sufficient activity for oxidation can be used, but are generally unnecessary and not desired.

In the reaction vessel, the polymers are broken down through chain scission into lower molecular weight organics and combustion products, with the product yield and distribution depending on the reaction parameters including temperature, pressure and reactant concentrations at the inlet, as well as the particular polymer which is being reacted. Generally for any particular polymer suitably amenable to the process, the relative amounts of oxidant, water and polymer, along with the inlet temperature and pressure, are optimized to promote carbon-carbon bond cleavage in the backbone of the polymer and to minimize other oxidation reactions, particularly complete oxidation to carbon dioxide and water. Accordingly, relatively small quantities of oxidant are used in the supercritical water reaction mixture in order to achieve partial, selective oxidation of the polymer to maximize monomer formation.

While lower molecular weight product distributions which optimize monomer yields are generally preferred, for any particular polymer the actual product distribution can be controlled by appropriate reactor design to vary the average residence time of the reactants and the residence time distribution, by appropriate selection of the oxidant to polymer molar or weight ratio, by appropriate choice of operating temperatures, pressures and concentration, by selecting an appropriate oxidation catalyst in some cases, and by controlling various other parameters such as the reactant to solvent ratio.

The depolymerization process in accordance with the invention generally occurs relatively rapidly and relatively short residence times are required as compared to, for example, heterogeneous catalytic oxidation processes. The residence times, like the other process parameters are dependent on the particular polymer being reacted and are selected to maximize monomer formation.

The depolymerization process can be carried out in a batch, semi-batch or continuous reaction system. Continuous stirred tank reactors, tubular flow reactors and fluidized bed reactors, among others, can be utilized with the process. The primary reactor design considerations being the ability to rapidly contact the reactants and handle the temperatures, pressures and corrosive effects of supercritical water solutions.

Because the reactions occur rapidly, heat losses are minimal and the products contain essentially all of the enthalpy of oxidation. Accordingly, in accordance with a preferred aspect of the invention, the enthalpy of oxidation can be recovered and used to preheat the reactants and to sustain the reactor temperature.

While the process can be used to depolymerize pure polymers, the process can also be used with polymers which have been blended or which otherwise incorporate normal quantities of conventional additives such as plasticizers, fillers, pigments and the like. The process can be used for separating the additives from the polymer and subsequently depolymerizing the polymer and also oxidizing organic type additives. Inorganic additives such as glass fibers, calcium carbonate and the like are generally insoluble in the supercritical water solution and can be recovered as a precipitated residue.

The invention thus provides a relatively simple process for recycling polymeric waste material to recover monomers and other useful low molecular weight components in a closed reaction system which is free of stack emissions to reduce land fill waste without generating air contaminants.

DETAILED DESCRIPTION OF THE INVENTION

Figure 1:
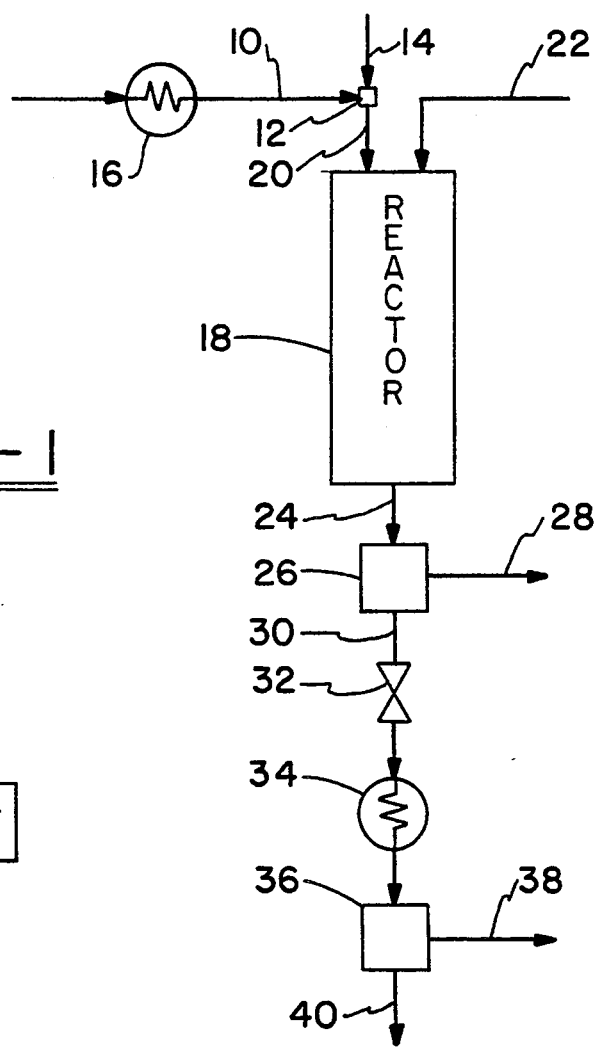
FIG. 1 is a schematic diagram of an apparatus for depolymerizing polymers in accordance with the principles of the invention.

The depolymerization process of the invention generally comprises the steps of forming a homogeneous or pseudohomogeneous mixture of polymer, water and oxidant, and causing the mixture to undergo selective oxidation at supercritical conditions for water to break up, i.e. depolymerize, the polymer into lower molecular weight components with a relatively high product yield of the monomer from which the polymer was originally polymerized. However, the depolymerization process of the invention can also be performed in accordance with the general principles of the invention at subcritical conditions but require longer reaction times. Other products generally include in progressively diminishing quantities dimers, trimers and other oligomers of the monomer, as well as small quantities of polymers, carbon dioxide, water and other combustion products depending on the polymer to be depolymerized.

The polymers can generally be prepared by step polymerizations (condensation polymerizations), wherein any two molecular species react with each other, or by chain polymerization, where an initiator species creates a reactive center (e.g. a free radical, an anion, or a cation) that adds monomer units in a chain reaction. In chain polymerization, the monomer can react only with the propogating reactive center and not merely with other monomers. The polymers and copolymers from chain polymerizations include those from halogenated vinyl monomers such as vinyl chloride, vinyl fluoride, tetrafluoroethylene, vinylidene chloride and vinylidene fluoride; acrylates and (alkyl)acrylates having a total of from 3 to 20, desirably from 3 to 8, carbon atoms such as methyl acrylate, methyl methacrylate, and ethylhexyl acrylate; acrylonitrile and substituted acrylonitriles having from 3 to 10 carbon atoms such as acrylonitrile and methacrylonitrile; aromatic substituted vinyl monomers having from 8 to 16 carbon atoms such as styrene, α-methyl styrene, and para-methyl styrene; vinyl acetate; and olefins having from 2 to 8 carbon atoms such as ethylene, propylene and isobutylene. Other polymers include those made from aldehydes having from 1 to 10 carbon atoms such as polyformaldehyde, polyacetaldehyde, polyvinyl alcohols and poly(alkylene oxides) having from 2 to 8 carbon atoms per repeat unit. Also included are metathesis polymers obtained from the ring-opening polymerization of cycloolefins catalyzed by transition metals. The cycloolefins have at least one unsaturated carbon-carbon bond and one or more rings and may desirably have from 5 to 20 carbon atoms.

The polymers from condensation polymerization include polyurethanes from aliphatic or aromatic polyisocyanates having from 3 to 24 carbon atoms, e.g. MDI, and molecules having two or more hydroxyl, carboxyl, amine and/or mercaptan groups reactive with the isocyanates. These molecules may be called polyols, polyacids, polyamines or polymercaptans if they have two or more of the respective reactive groups. They can desirably have molecular weights from about 50 to 10,000 or 15,000 and be polymers of polyester, poly(alkylene oxides) etc. Other polymers include various polyamides, various polyesters, various melamine-formaldehyde resins, various phenol-formaldehydes, various polycarbonates and the like.

Preferred polymers include polyvinyl chloride, polyethylene, polycarbonate, polystyrene and polyvinyl acetate.

The polymers used can be crosslinked or may be linear polymers with a wide range of molecular weights such as from about 5,000 to as high as 300,000 or several million. However, the effectiveness decreases with high amounts of crosslinking.

A wide range of polymer having diverse molecular weights can be processed in accordance with the invention, including low molecular weight polymers at or near the oligomer range up to and including high molecular weight polymers of a highly crystalline character. The polymeric materials which can be depolymerized include those containing various amounts of conventional additives such as antimicrobials, antioxidants, antistatic and static dissipative agents, color concentrates, colorants and pigments, emulsifiers, fillers, flame retardants, foaming agents, fragrances, heat stabilizers, impact modifiers, lubricants, mold release agents, plasticizers, reinforcing fibers, smoke suppressants, ultraviolet stabilizers, viscosity depressants and other rheological modifiers, and the like.

The oxidant or oxidizing agent is preferably air, oxygen, or a mixture of oxygen and inert gases, but other oxidants such as peroxy compounds or oxygen generating species such as peroxides, e.g. hydrogen peroxide, ozone; dicumyl peroxide, etc. perchlorate, permanganates, such as a potassium permanganate, and the like can be used including any compounds known to generate or release oxygen at reaction conditions. A conventional oxidation catalyst can also be used.

The relative amounts of water, polymeric material and oxidant is dependent upon the particular polymer or polymers which are being depolymerized via the selective, oxidative depolymerization process of the invention and on the desired product distribution, e.g. molecular weight distribution of the products. Generally, however, low amounts of oxidant combined with short residence time are utilized so as to promote or maximize carbon-carbon bond breakage or cleavage and to inhibit or limit other undesirable reactions such as complete oxidation to carbon dioxide and water. In other words, oxidant used is regulated such that the reaction is carried out to only a partial extent so as not to completely oxidize the end product. The exact amount of oxidant in the form of oxygen can vary over a wide range as from about 0.5 percent to about 95 percent by volume based upon the total volume of supercritical water and oxygen or oxidant, and the polymer. Generally, low amounts of oxygen such as from about 0.5 to about 30 percent, and more desirably from about 5 to about 15 percent, by volume based upon the total volume of supercritical water, the oxidant, and polymeric material used.

The reaction is generally carried out at a temperature and at a pressure above the critical temperature (about 647° K.) and critical pressure (about 218 atmospheres) of water; however, conditions near to the critical conditions can also be used but are generally less effective.

The amount of polymeric material used relative to the amount of water in the reaction mixture can also vary depending on the particular polymer being depolymerized and on the other operating parameters such as temperature, pressure and oxidant concentration and chosen residence time. The amount of polymer used is further restricted by the energy balance. That is, the total amount of polymer used must be such that the temperature rise generated by the exothermic reaction is less than the maximum temperature needed to melt the oxidation vessel. This constraint depends on the polymer weight, the heat of combustion associated with the particular polymer, the amount of oxidant used, the reactor pressure and the reaction starting temperature. However, the amount of polymeric material used in the reaction mixture is generally near the maximum amount which can be solubilized by or added to the supercritical water without losing the homogeneous single fluid phase character of the mixture. The maximum amount of polymeric material which can be mixed into a given quantity of supercritical water can also be limited in some cases by the tendency of intermediate products of the selective oxidation process to react either with the polymer, the oxidant and/or other intermediate products of the reaction to produce significant quantities of undesirable by-products. Typically, the amount of polymer which can be added to the critical water to form the reaction mixture can range from about 1 percent to about 50 percent, and more preferably from 10 percent to 30 percent of the weight of the water and polymer combined.

The reaction time or residence time in the reactor depends upon various factors such as the amount of oxygen, the temperature and pressure of the reaction mixture, oxidant and polymer concentration in the reaction mixture, and the like, and can generally range from about 3 seconds to about 1 hour. Most of polymeric materials can be processed within a residence time of 3 minutes. The residence time also depends upon the desired product distribution. Generally speaking, a long residence time tends to cause more $CO_2$ and $H_2O$ in the product, while a short residence time causes more monomers in the product distribution. However, if it is too short, then the total process yield decreases. The amount of carbon dioxide produced during the process is generally less than 20 percent, desirably less than 10 percent, and most preferably less than 5 percent by volume.

Typical products from the process include monomers, dimers, trimers, oligomers having up to about 8 repeat groups, carbon dioxide, water and halide acids (when the base polymer includes halogens). Trace amounts of methane, ethane, ethylene and higher hydrocarbons (up to $C_5$) are also obtained depending on the specific operating conditions. Typical monomer and dimer yields from the process range from 10 to 90 percent by mass of the original base polymer. More specifically, the process is capable of attaining monomer yields of at least 5 percent, and more desirably at least 40 or 50 percent, and most preferably 60, 70 or 80 percent based on the theoretical maximum monomer yield for the particular polymer being depolymerized. The theoretical maximum monomer yield is the number of monomers which were used to actually produce the polymer or the number of monomer units which could have theoretically been used to produce the polymers.

Typical operating conditions are:
Temperature = 374°–500° C., preferably 380° to 450° C.
Pressure = 218–400 atm, preferably 220 to 270 atm
Mode: Continuous, batch, semi-batch
Feed: Premixed or in-situ mixed However, the process can also be operated at subcritical conditions, with or without a catalyst. The conditions are:
Temperature = 200°–374° C., preferably 300°–374° C.
Pressure = 70–218 atm, preferably 150–218 atm Depolymerization at subcritical conditions are generally not preferred, however, because they require larger residence times and/or result in lower product yields and lower product selectivity.

There is shown in FIG. 1 a simplified schematic representation of apparatus useful for practicing of the invention in a continuous process mode. The polymer or polymeric feed material containing polymer along with additives and/or other impurities is carried through conduit means 10 to mixing point 12 where it is preferably thoroughly mixed with water carried through conduit means 14. The polymer is preferably comminuted, for example, to a particle size of from about $0.5\mu$ to 5 cm, and desirably from about 10 to about 200 microns, and is also preferably mixed with water to form a pumpable slurry. The polymer can optionally be preheated at preheater 16 using thermal energy recovered downstream in the process. The water which is mixed with the polymer is generally at a temperature and pressure near or above the critical temperature and pressure of water and preferably at a temperature and pressure sufficient to ensure that the reaction mixture is at least sufficiently near the critical conditions for water to ensure that critical conditions are reached in the reactor 18 upon the evolution of heat from the exothermic oxidation reactions. Most preferably, the temperature and pressure of the water carried in conduit means 14 are sufficiently high to ensure that the reaction mixture comprising the polymer or polymeric material, along with additives and/or other impurities carried through conduit means 10 mixed with the water from conduit means 14 and entering reactor 18 through conduit means 20 are at or above the critical temperature and pressure of water. At or immediately prior to the inlet of the reactor an oxidant carried through conduit means 22 is mixed with the reaction mixture carried through conduit means 20. The reaction mixture and oxidant are preferably mixed with sufficient turbulence or mechanical agitation to ensure thorough macroscopic homogeneity of the polymer, oxidant and solvent. The reactor 18 can, for example, be a plug flow reactor of sufficient length to provide for optimum conversion of the polymer to useful low molecular weight components, especially optimum conversion or product yield of the monomer from which the polymer either was or could have been polymerized.

Inorganic additives and/or impurities carried with or contained within the polymeric feed material generally become separated from the polymer in the reactor. Because inorganic materials are not generally soluble in the supercritical fluid mixture, any inorganic materials entering the reactor with the polymer are precipitated within the reactor and can be separated as a solid residue from the reactor outlet stream 24 at separator 26 and removed via conduit or conveyance means 28. Separator 26 can generally be any suitable conventional apparatus for separating solids from a fluid such as filtering or centrifuge means.

Organic additives and/or impurities can also be handled by the apparatus of the invention. Generally, such organic additives or impurities will be oxidized and converted to lower molecular weight fragments and components which are carried along with the products and byproducts in the fluid phase exiting from separator 26.

The reaction products in the fluid phase exit separator 26 via conduit means 30 and pass through pressure reducing means 32 which lowers the pressure of fluid to near ambient pressure. The fluid then flows into condenser 34 wherein the water is condensed to the liquid phase.

Separator 26 can be eliminated in the event that polymers or polymeric materials having relatively low amounts of inorganic precipitatable additives or impurities are being recycled. Alternatively, solids and/or precipitated materials can be separated from the product stream downstream of the process.

In general, the liquid water and the organic products are generally immiscible and can be easily separated by conventional gas-liquid or liquid-liquid separating means 36 depending on the polymer depolymerized and the resulting products. The product stream 38 containing the desired monomer can be subjected to various known unit operations, such as distillation, solvent extraction, chilling, etc. depending on the nature of the products, in order to achieve the desired degree of purity of the monomeric component. The water stream can be suitably reheated and repressurized for reintroduction into the process via conduit means 14.

In accordance with a preferred aspect of the invention, heat removed from the process at condenser 34 can be recovered and used for preheating the polymer at preheater 16 and/or used for heating the water used as a solvent in the process.

The high temperatures, generally in excess of 374° C., and high pressures, generally in excess of 218 atmospheres, along with the corrosive nature of supercritical water, but more importantly subcritical water must be taken into consideration when designing the process apparatus for practicing the invention. In particular, Hastelloy C-276 has been found to be a suitable material for the construction of the reactor vessel and various other apparatus exposed to the supercritical water and/or reaction mixture and any wetted part which is exposed to subcritical water during start-up and shutdown.

The process can be used to recycle various waste end products such as waste from molding operations, extrusion operations, and the like, instead of being disposed in accordance with stringent EPA requirements. The recovered monomers can then be returned to the polymer manufacturing facilities to create virgin polymers. The depolymerization process generally yields in excess of 80 percent, and preferably in excess of 90 percent, monomer recovery based on the weight of the monomers originally used to form the polymer which is depolymerized by the process of the invention. By suitably adjusting parameters, the process can also be utilized to achieve higher product molecular weight distributions, such as to maximize dimer, trimer or other oligomer products, and for converting polymers such as, for example, polyolefins to fuels or lubricants which can be used as a substitute for oil or gasoline.

The invention will be further illustrated by, but is not in any way limited by, the following examples and pilot plant apparatus used in association with the examples.

Figure 2:
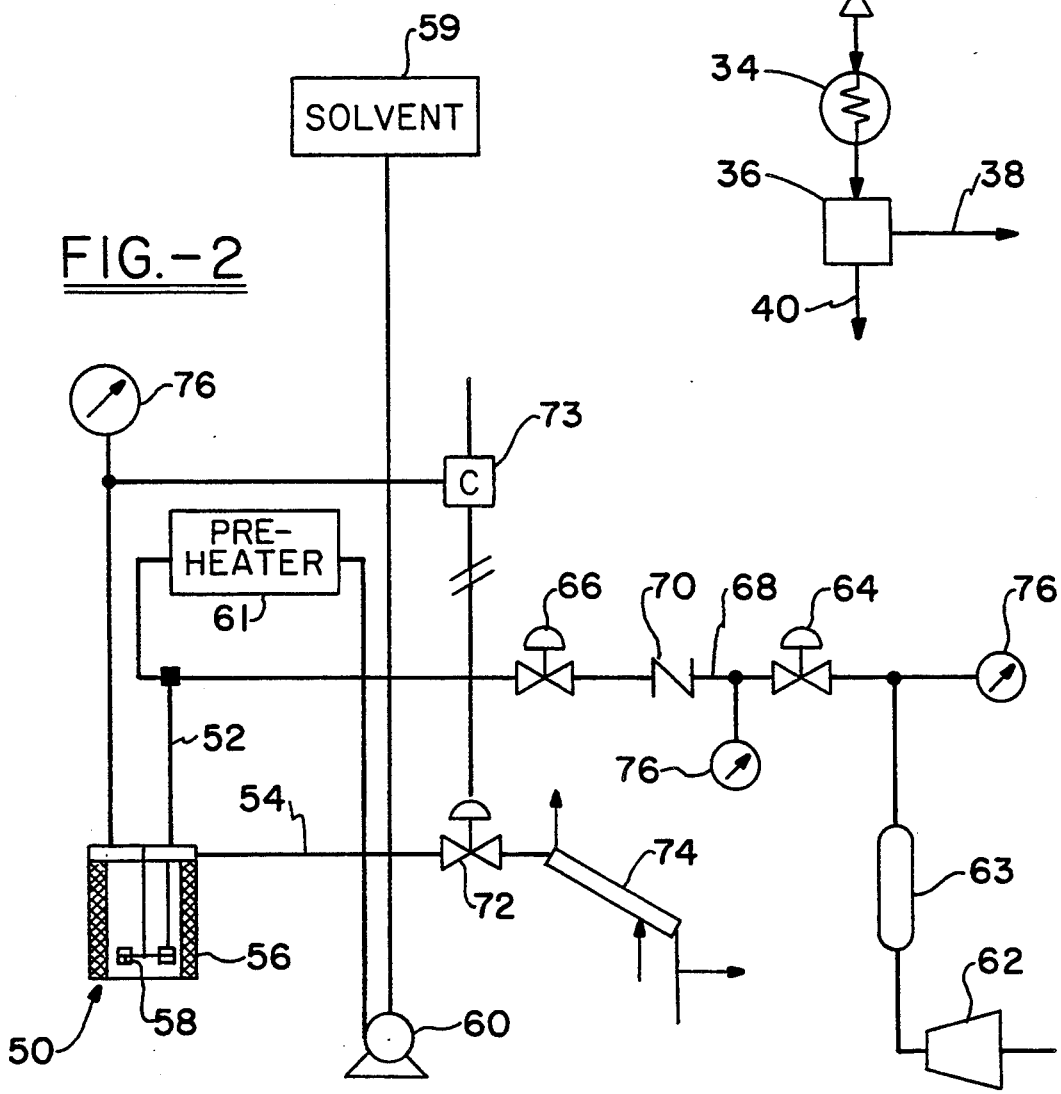
FIG. 2 is a schematic of a pilot scale apparatus for depolymerizing polymers in accordance with the principles of the invention.

FIG. 2 is a schematic representation of an apparatus used to study and verify the oxidative depolymerization process for depolymerizing polymers. The system consists of three sections, an electrically heated oxidation vessel, a high pressure solvent delivery system, and a water cooled depressurization and collection chamber.

BOLT CLOSURE REACTOR

The oxidative depolymerization vessel 50 depicted in FIG. 2 is a high pressure, 1000 cc Hastelloy C-276 steel bolt closure reactor manufactured by Autoclave Engineers Inc. The unit is fitted with $\frac{1}{8}''$ and $\frac{1}{4}''$ Hastelloy C-276 feed delivery 52 and product outlet lines 54 respectively. The reactor is equipped with a thermowell (not shown), cooling coil (not shown), a top-mounted, air-driven agitator 58 (magnedrive) and a heating jacket 56 for start-up.

SOLVENT DELIVERY SYSTEM

Water is delivered from a solvent reservoir 59 to the reactor via a high pressure micro-metering pump 60. This is capable of precisely delivering the solvent against a 5000 psi back pressure. A preheater 61 is provided to heat the water to a temperature sufficiently near the critical temperature to ensure that critical conditions are reached in the reactor. The flow capacity of this unit is 6000 cc (RTP)/hr at a motor speed of 85 RPM.

Oxygen is delivered to the reactor by a high pressure oxygen compressor 62 (Haskel AGT 30/75) via high-pressure oxygen storage cylinder 63. This air driven unit is capable of pressurizing pure oxygen to a maximum pressure of 5000 psi. The compressor is also equipped with a variable pressure safety relief valve and an automated air pilot switch. Both these safety features make it practically impossible to over-pressurize the oxygen storage cylinder 63, thereby decreasing the chances of failure due to spontaneous oxidation caused by over-pressurization of the components. A pressure regulator valve 64 and flow controller 66 are provided in the oxygen feed line 68. A check valve 70 is also provided in the oxygen feed line to prevent water from entering the oxygen storage cylinder 63 in the event of an unexpected loss of pressure. Gauges 76 are provided as appropriate to monitor pressure in the apparatus.

PRODUCT DEPRESSURIZATION

Depressurization of the oxidation unit is done with the use of a high pressure control valve 72. A pneumatic controller 73 is used to operate in any one of the control actions; proportional, reset or derivative. Following the control valve, the hot products are directed to a water cooled high pressure condenser 74. Here they are cooled to ambient conditions before being sent to a holding vessel for GC analysis.

In the absence of oxygen, the thermal degradation of polyvinyl chloride involves dehydrochlorination, which gives polyene sequences followed by crosslinking. The dehydrochlorination also takes place even in the presence of oxygen or in other oxidative environments. When oxygen is present, chain scissions involving C—C bond breakages as well as dehydrochlorination take place. The relative rates of these two modes of reactions depend upon the concentration of oxygen, the temperature, the pressure in the case of supercritical oxidative depolymerization, etc.

In the supercritical oxidative depolymerization, the concentration of oxygen in the reactive system is high and the contact between the reactants is more intimate, thus making chain scission reactions much more active. This appears to be a major reason for more rapid degradation of PVC in an oxygen environment and production of monomers and dimers.

The depolymerization of PVC is believed to proceed in accordance with the following reaction mechanisms. These reaction mechanisms have not been conclusively verified but are consistent with the species identified in the reaction product streams when PVC is reacted in accordance with the process of the invention.

I. Dehydrochlorination and Oxidation

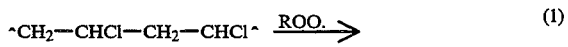
(1)

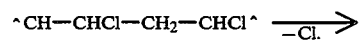

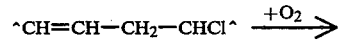

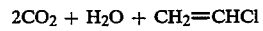

$$2CO_2 + H_2O + CH_2=CHCl$$

The dehydrochlorination rate is believed to increase substantially in a oxidative depolymerization environment due to peroxy radicals, which are formed by the straight oxidation of a hydrocarbon or a fraction of the polymer.

II. Dehydrochlorination and Chain Scissions

(2)

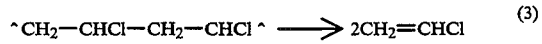
(3)

(4)

-continued $$CH_2=C(Cl)-CH=CHCl + H_2$$

III. Oxidation $$^\wedge CH_2-CHCl-CH_2-CHCl^\wedge \xrightarrow{ROO\cdot} \quad (5)$$

$$^\wedge CH-CHCl-CH_2CHCl^\wedge \xrightarrow{-Cl\cdot}$$

$$^\wedge CH=CH-CH_2-CHCl^\wedge \xrightarrow{-HCl,\ -Cl\cdot}$$

$$^\wedge CH=CH-CH=CH^\wedge \xrightarrow{+O_2} CO_2 + H_2O$$

$$CH_2=CHCl + 5/2\, O_2 \longrightarrow 2CO_2 + H_2O + HCl \quad (6)$$

The final products of Route III are $CO_2$, $H_2O$, and HCl in their stoichiometric amounts.

IV. Hydrochlorination $$CH_2=CHCl + HCl \rightarrow CH_2Cl-CH_2Cl \quad (7)$$

$$CH_2=CHCl + HCl \rightarrow CH_3-CHCl_2 \quad (8)$$

$$CH_2=CH-CH=CH_2 + 2HCl \rightarrow CH_3-CHCl-CHCl-CH_3 \quad (9)$$

It is believed that all of these reactions included in Routes I, II, III, and IV, take place competitively in the system, even though their relative kinetic rates depend on various operating parameters, in particular, the oxygen concentration, the reactor residence time, and the process pressure and temperature. In accordance with the principles of the invention, the most dominant reactions at or near supercritical conditions are believed to be (1), (7), and (8), resulting in high yields of vinyl chloride monomer (VCM), 1,1-dichloroethane and 1,2-dichloroethane. The formation of 1,1-dichloroethane is more dominating than 1,2-dichloroethane. For example, if the reaction mixture is left too long in a oxidative depolymerization environment, the reaction would proceed to completion, resulting in producing only $H_2O$, $CO_2$, and HCl. Therefore, in order to maximize the production of vinyl chloride monomer or dimers, an optimal process condition must be sought after, especially in terms of the residence time, percent excess of oxygen, temperature, and pressure.

EXAMPLE 1

Selective partial oxidative depolymerization of polyvinyl chloride (PVC) was performed using the oxidative depolymerization pilot plant described in earlier sections. Experiments were initiated by charging the primary oxidation vessel with a preweighed amount of PVC resin. A typical oxidation utilized 0.5 to 20 g of PVC. Once charged, the oxidation vessel was brought up to the desired extraction temperature and pressure by heating and the constant addition of preheated supercritical water. Oxidation temperatures ranged between about 388° and about 443° C. with pressures ranging from about 231 to about 273 atmospheres. Once the operating parameters were established, the injection of high pressure oxygen was initiated. Oxygen flow rates ranged between 50 and 2000 scc/min. Reactor effluents were then collected at preset intervals and were directed to a gas chromatograph for analysis.

Figure 3:
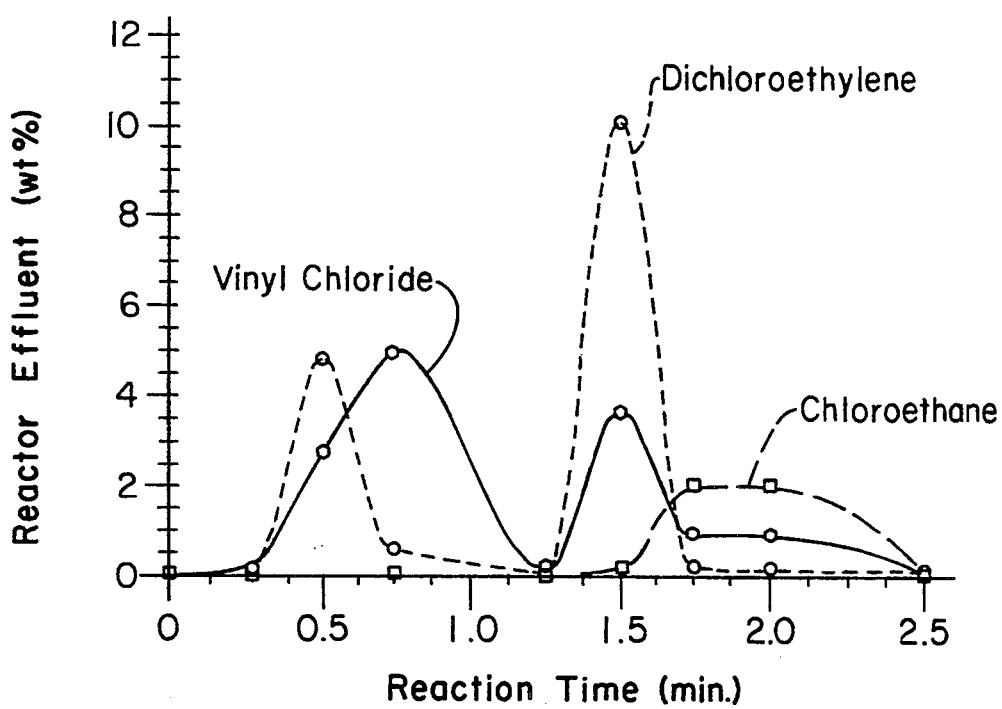
FIG. 3 shows the rate of production curves of vinyl chloride, chloroethane and dichloroethylene for the oxidative depolymerization of polyvinyl chloride.
Figure 4:
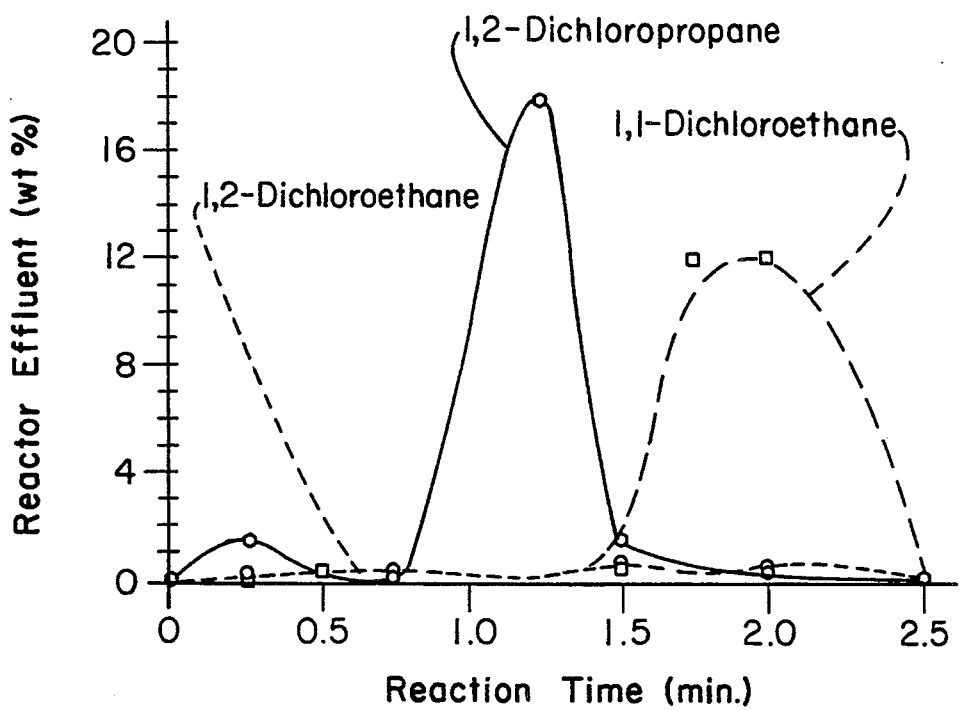
FIG. 4 shows the rate of production curves of 1,2-dichloropropane, 1,1-dichloroethane and 1,2-dichloroethane for the oxidative depolymerization of polyvinyl chloride.
Figure 5:
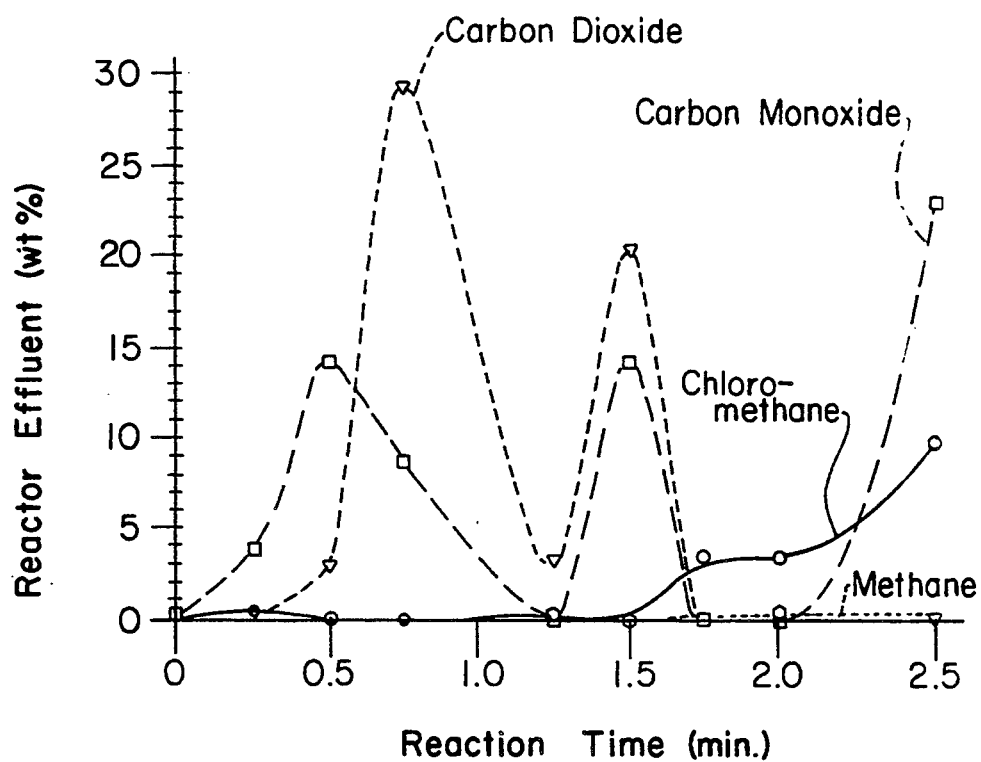
FIG. 5 shows the rate of production curves of chloromethane, carbon monoxide, methane and carbon dioxide for the oxidative depolymerization of polyvinyl chloride.
Figure 6:
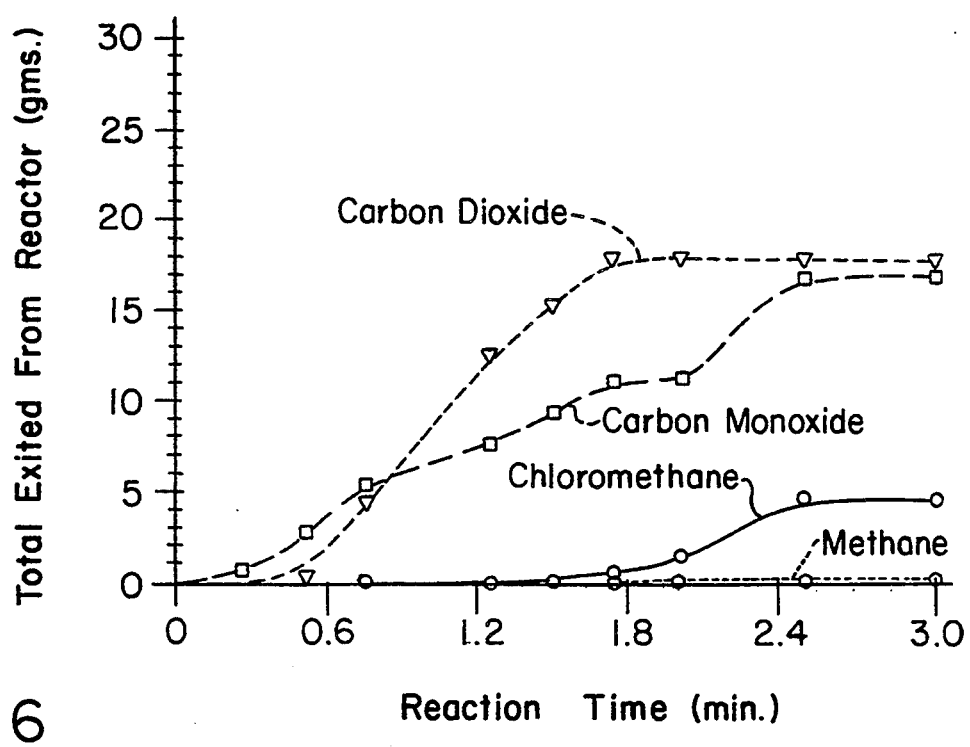
FIG. 6 shows the integral or cumulative plot of the effluent gas stream for chloromethane, methane, carbon monoxide and carbon dioxide for the oxidative depolymerization of polyvinyl chloride.
Figure 7:
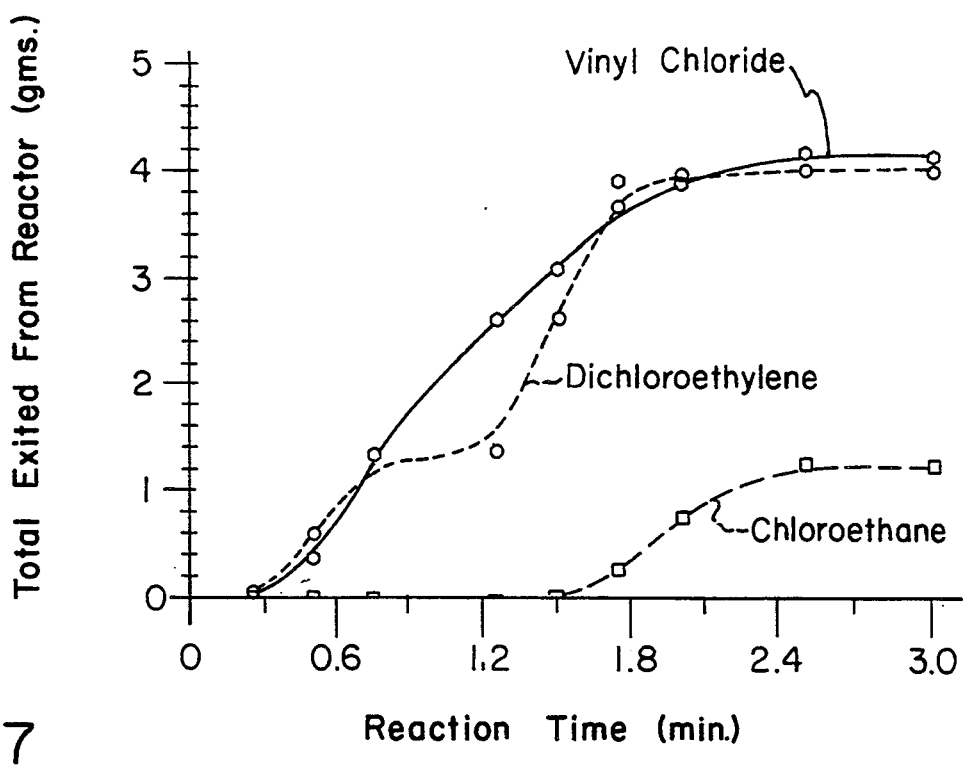
FIG. 7 shows the integral or cumulative plot of the effluent gas stream for vinyl chloride, chloroethane and dichloroethylene for the oxidative depolymerization of polyvinyl chloride.
Figure 8:
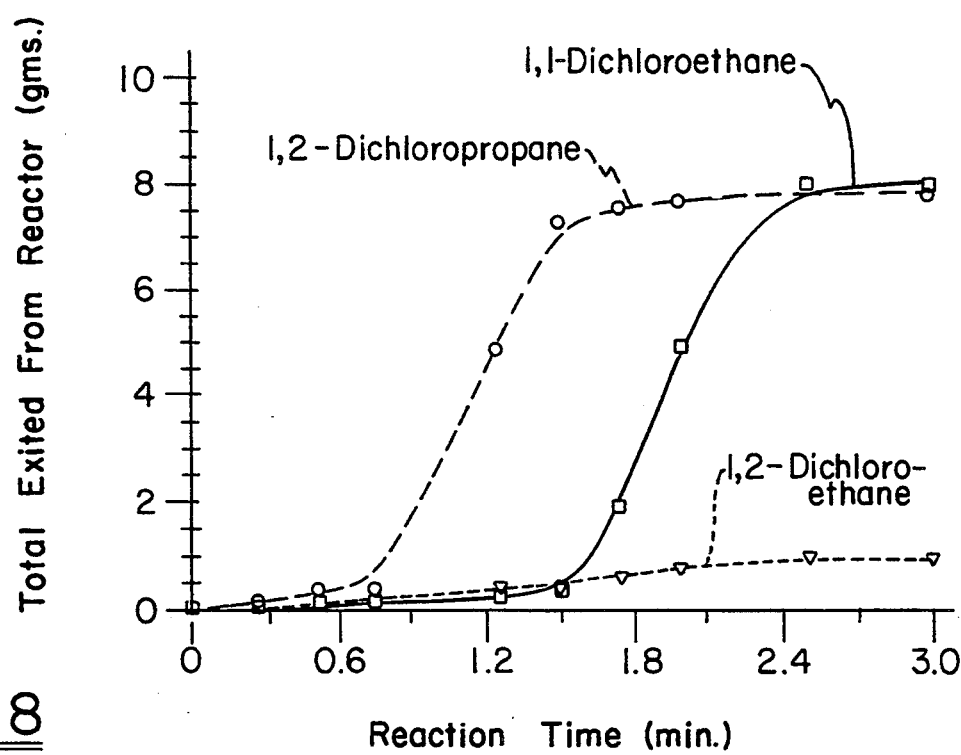
FIG. 8 shows the integral or cumulative plot of the effluent gas stream for 1,2-dichloropropane, 1,1-dichloroethane and 1,2-dichloroethane for the oxidative depolymerization of polyvinyl chloride.

FIGS. 3–5 show the rate of production of various depolymerization products as a function of reaction time for the oxidative depolymerization of polyvinyl chloride in accordance with the invention, and FIGS. 6–8 show the integral or cumulative total production as a function of reaction time.

EXAMPLE 2

Isotactic polypropylene (PP) is depolymerized selectively in the oxidative depolymerization pilot plant system, at 383° C. and 232 atm.

Figure 9:
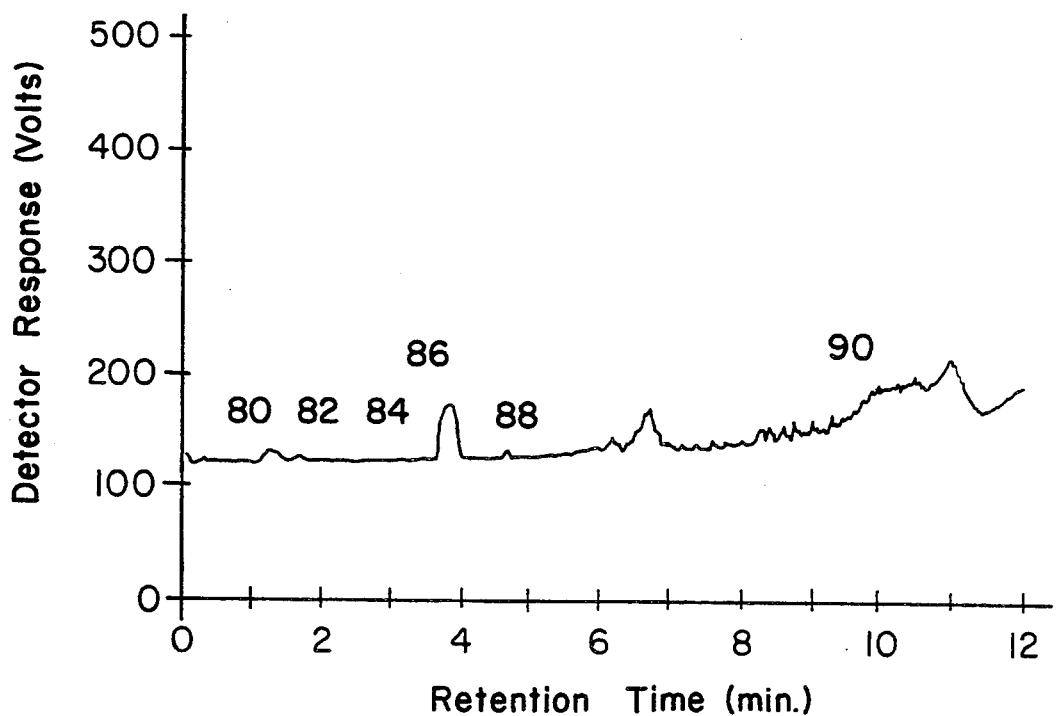
FIG. 9 shows the gas chromatograph analysis of the gas stream from the oxidative depolymerization of polypropylene.

A typical amount of PP used ranges from 0.5 to 20 grams, with oxygen flow rates of 50 to 2000 scc/min. The resultant product distribution includes 6 major chemical species identified by FID (Flame Ionization Detector) on a gas chromatograph. The most dominant species were propylene 86, methane 80, ethylene 82, and acetic acid 84, as shown in FIG. 9 of the gas chromatograph spectrum.

The typical monomer yield ranges from 5 to 65 percent by mass of the original base polymer. The residence time depends on the flow rate of input oxygen and other operating parameters, and typically ranges from 10 seconds to 5 minutes. Higher concentration of oxygen generally shortens the retention time, however, decreases the monomer selectivity.

The pH of the reactor residual water was 3.2, mostly coming from acetic acid.

EXAMPLE 3

Homopolymer polystyrene (PS) was depolymerized selectively in the oxidative depolymerization system, at 383° C. and 232 atm.

Figure 10:
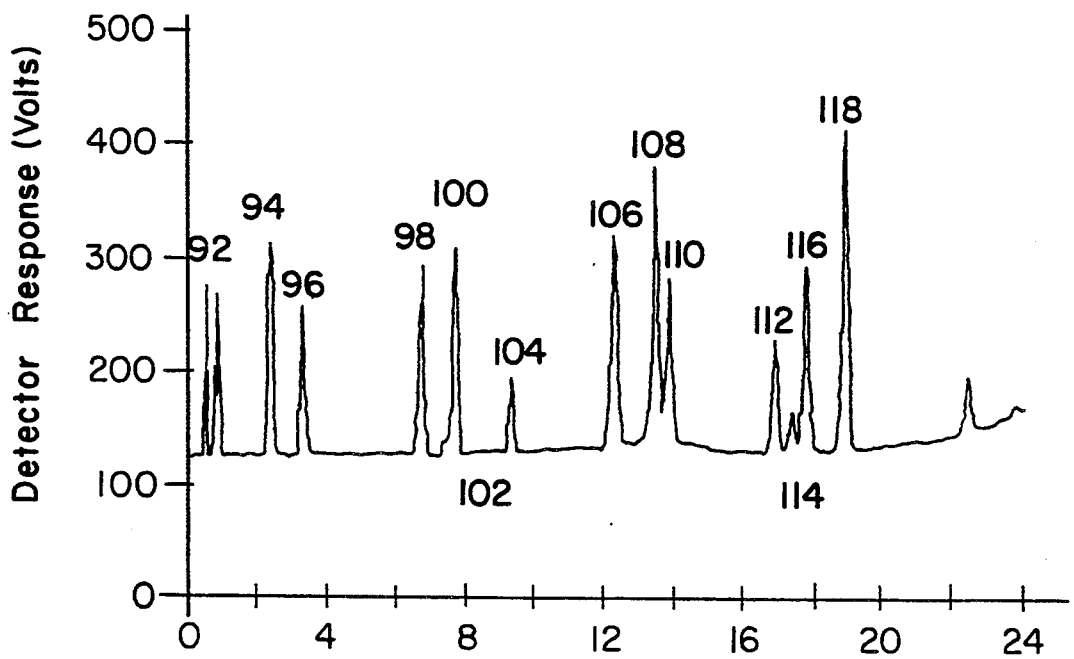
FIG. 10 shows the gas chromatograph analysis of the gas stream from the oxidative depolymerization of polystyrene.

A typical amount of PS used ranges from 0.5 to 20 grams, with oxygen flow rates ranging between 50 and 2000 scc/min. The resultant product distribution includes a much wider spectrum of various light hydrocarbon species, as shown in FIG. 10.

The typical products include: Methane, ethylene, propylene, isobutylene, propane, butane, benzene, toluene and styrene monomer, etc. Styrene monomer exist in both liquid and vapor phase, as evidenced by styrene detected in the reactor residual water. By controlling the operating parameters, i.e., temperature, pressure, reaction time, oxygen concentration, the product distribution can be controlled to give a stream with a product distribution from $CO_2$-rich, to light hydrocarbon-rich, to styrene-rich and benzene-rich cases.

Typical retention time ranges from 10 seconds to 5 minutes, preferably 30 seconds to 2 minutes. Typically, a shorter reaction time favors aromatic monomer formations, i.e., styrene and ethyl benzene.

EXAMPLE 4

Figure 11:
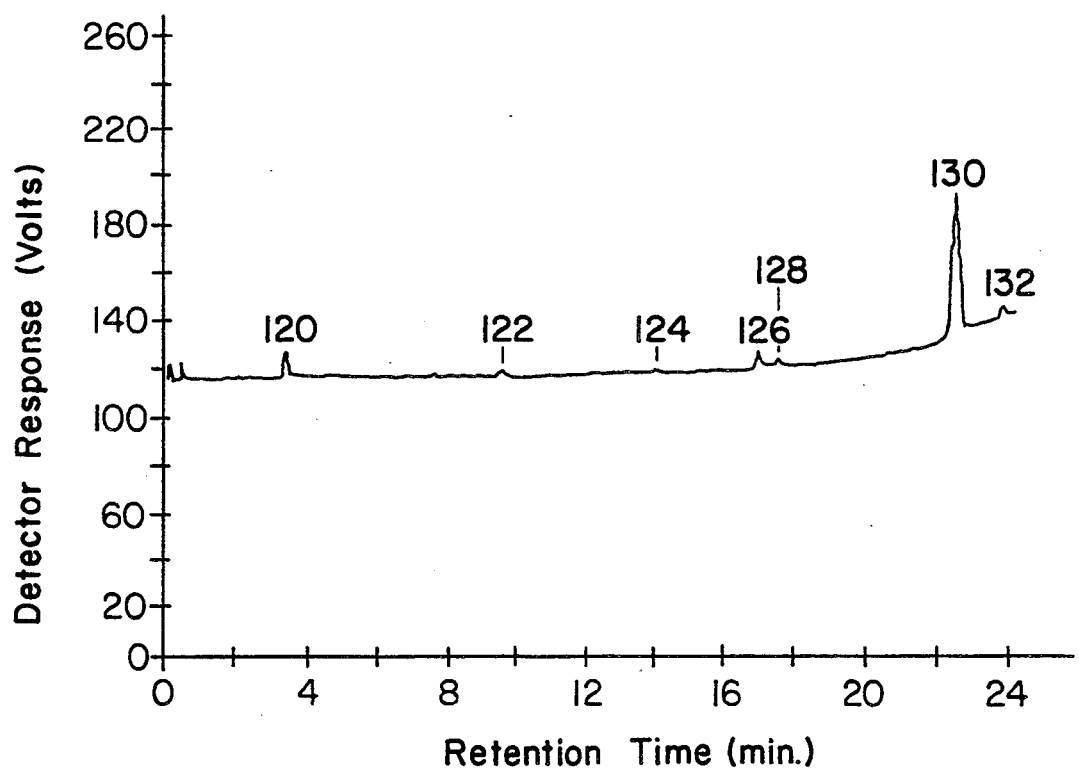
FIG. 11 shows the gas chromatograph analysis of the gas stream from the oxidative depolymerization of polypropylene when the reaction is run at 383° C., 3400 psig, with 180 sccm of oxygen for 15 seconds.
Figure 12:
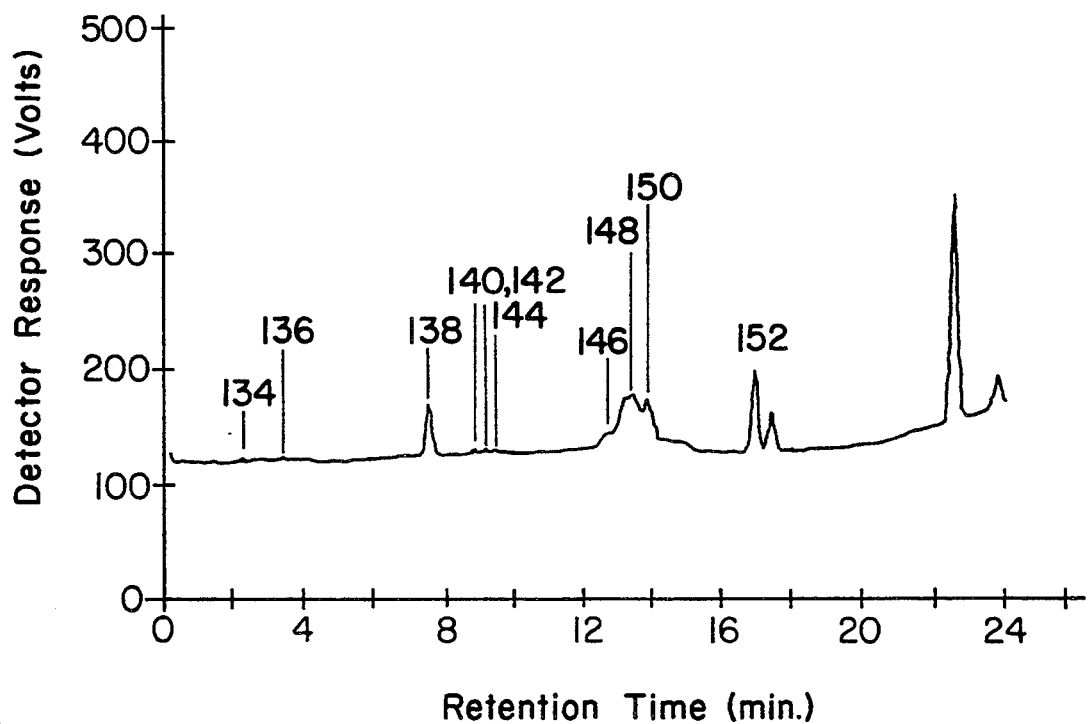
FIG. 12 shows the gas chromatograph analysis of the gas stream from the oxidative depolymerization of polypropylene when the reaction is run at 413° C., 3800 psig, with 90 sccm of oxygen for 30 seconds.
Figure 13:
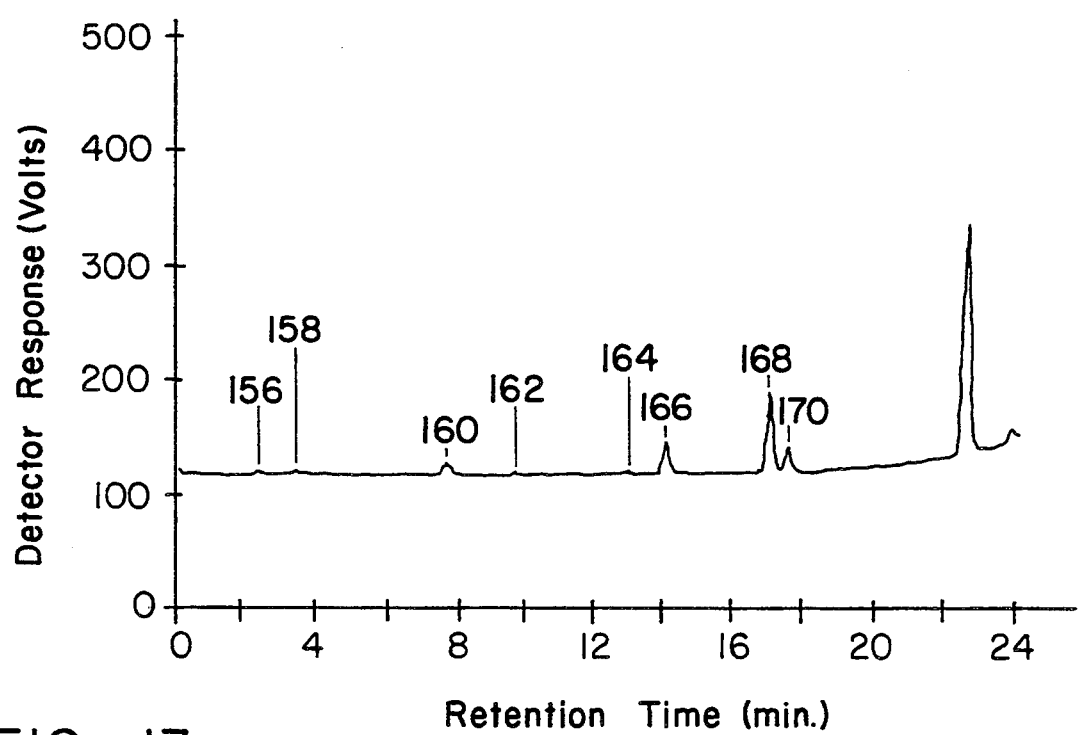
FIG. 13 shows the gas chromatograph analysis of the gas stream from the oxidative depolymerization of polypropylene when the reaction is run at 413° C., 3600 psig with 90 sccm of oxygen for 30 seconds.

Three additional depolymerization runs were made. The run conditions were at (a) 383° C., 233 atmospheres, 180 sccm oxygen for 15 sec. (see chromatogram at FIG. 11); (b) 413° C., 260 atmospheres, 90 sccm oxygen for 30 sec. (see chromatogram at FIG. 12); and (c) 413° C., 246 atmospheres, 90 sccm oxygen for 30 sec. (see chromatogram at FIG. 13). Each experimental data set gave markedly different chromatograms as can be seen in FIGS. 11–13, which are the FID area counts and chromatograms. Propylene itself comes off at 2.4 minutes as calibrated previously, this appears in small amounts in runs (b) and (c). The other peaks at this time have not been identified. These graphs show the product distribution changes that occur by running at different conditions.

As shown in Table I, the product distributions for runs (a), (b) and (c) are quite dissimilar, especially (a) and (b). [(b) and (c) are somewhat similar to each other.] The basic differences are:

(1) At lower temperatures, PP breaks down to hydrocarbons, less oxygenated, while at higher temperatures more oxygenated hydrocarbon species are produced.

(2) Product concentrations are also quite varying depending on the process conditions.

(3) In run (a), there is no propylene produced, whereas in (b) and (c), small amounts of propylene are produced.

TABLE I

| PEAK # | COMPONENT | PEAK AREA |
|---|---|---|
| Run (a), 383° C., 233 atm., 180 sccm, 15s | | |
| 120 | Isopropanol | 105 |
| 122 | Isopentane | 60 |
| 124 | 2,3-dimethyl-butane | 35 |
| 126, 128 | Methylhexane | 74, 26 |
| 130 | Unidentified | 492 |
| 132 | Unidentified | 49 |
| Run (b), 413° C., 260 atm., 90 sccm, 30s | | |
| 134 | Propylene | 77 |
| 136 | Acetone | 44 |
| 138 | 3-hydroxy-2-butanone | 702 |
| 130, 142, 144 | Isopentanone; 2,3-dimethylbutane; 3-methoxy-2-butanone | 59, 64, 34 |
| 146, 148, 150 | 2-hexanone; 4-methyl-3-penten-2-one | 205, 1839, 606 |
| 152 | 5-methyl-2-hexanone | 571 |
| Run (c), 413° C., 246 Atm., 90 sccm, 30s | | |
| 156 | Propylene | 52 |
| 158 | Acetone | 23 |
| 160 | 2,3-butanedione | 149 |
| 162 | 2-pentanone | 29 |
| 164, 166 | 4-methyl-2-pentanol | 24, 338 |
| 168, 170 | 5-methoxy-2,3-hexanedione | 832, 287 |

The yield of lower molecular weight components, i.e. having 3-7 carbon atoms, is 85 percent, 45 percent and 50 percent by weight based on the original weight of the polymer for runs (a), (b) and (c), respectively.

By this experiment, it is demonstrated:

(1) The product distribution and their concentration can be controlled to a good degree.

(2) The production of propylene or monomer from polymer is not scientifically obvious.

(3) T,P, flow rate, reaction time, and system design also affect the process output.

While in accordance with the Patent Statutes, a preferred embodiment and best mode has been presented, the scope of the invention is not limited thereto, but rather is measured by the scope of the attached claims.

What is claimed:

1. A process for depolymerizing polymeric material to obtain high product yields of low molecular weight compounds, the process comprising the steps of:
   a) forming a reaction mixture of polymeric material, water at or near supercritical conditions, and an oxidant; and
   b) reacting the mixture at or near the supercritical condition for water to effect selective partial oxidation of the polymer contained within the polymeric material.

2. A process according to claim 1, wherein the polymeric material comprises an addition polymer having a strong electron withdrawing group.

3. A process according to claim 2, wherein the electron withdrawing group is a halogen, nitrile, hydroxyl, phenyl, carboxyl or ester group.

4. A process according to claim 1, wherein the polymeric material is a polyolefin, polyvinyl chloride, polyvinylidene chloride, polyvinyl fluoride, polyvinylidene fluoride, polyacrylate or polyalkyl acrylate, polyacrylonitrile, polycarbonate, polycyclic olefin, polyurethane, polymethacrylate, polyacetaldehyde, polyformaldehyde, polystyrene, or polymethylmethacrylate.

5. A process according to claim 1, wherein the polymeric material is polyvinyl chloride, polyethylene, polycarbonate, polystyrene or polyvinyl acetate.

6. A process according to claim 1, wherein the reaction is carried out at a temperature in excess of 200° C. and at a pressure in excess of 70 atmospheres.

7. A process according to claim 1, wherein the reaction is carried out at a temperature in excess of 374° C. and at a pressure in excess of 218 atmospheres.

8. A process according to claim 5, wherein the reaction is carried out at a temperature between about 380° C. to 450° C. and at a pressure between about 220 to 270 atmospheres.

9. A process according to claim 8, wherein the oxidant is oxygen and the amount utilized is from about 0.5 percent to about 30 percent by volume based upon the total volume of the supercritical water, the oxidant and the polymeric material.

10. A process according to claim 9, wherein the polymeric material is processed within a residence time of 3 minutes.

11. A process according to claim 10, wherein the monomer yield is in excess of 45 percent of the theoretical maximum monomer yield.

12. A process according to claim 1, further comprising the step of comminuting the polymeric waste material and mixing it with a fluid to form a pumpable composition, before forming the reaction mixture.

13. A process according to claim 12, further comprising the step of preheating the pumpable composition prior to forming the reaction mixture.

14. A process according to claim 13, wherein the polymeric waste material contains inorganic additives, and further comprising the steps of precipitating the inorganic materials from the reaction mixture and separating the precipitated materials from the reaction products.

15. The reaction product of a process for depolymerizing polymeric material to obtain high product yields of low molecular weight compounds, the process comprising the steps of:
   a) forming a reaction mixture of polymeric material, water at or near supercritical conditions, and an oxidant; and
   b) reacting the mixture at or near supercritical conditions for water to effect selective partial oxidation of the polymer contained within the polymeric material.

16. The reaction product of claim 15, wherein the polymeric material comprises an addition polymer having a strong electron withdrawing group.

17. The reaction product of claim 16, wherein the electron withdrawing group is a halogen, nitrile, hydroxyl, phenyl, carboxyl or ester group.

18. The reaction product of claim 15, wherein the polymeric material is a polyolefin, polyvinyl chloride, polyvinylidene chloride, polyvinyl fluoride, polyvinylidene fluoride, polyacrylate or polyalkyl acrylate, polyacrylonitrile, polycarbonate, polycyclic olefin, polyurethane, polymethacrylate, polyacetaldehyde, polyformaldehyde, polystyrene, or polymethylmethacrylate.

19. The reaction product of claim 15, wherein the polymeric material is polyvinyl chloride, polyethylene, polycarbonate, polystyrene or polyvinyl acetate.

20. The reaction product of claim 15, wherein the reaction is carried out at a temperature in excess of 200° C. and at a pressure in excess of 70 atmospheres.

21. The reaction product of claim 15, wherein the reaction is carried out at a temperature in excess of 374° C. and at a pressure in excess of 218 atmospheres.

22. The reaction product of to claim 18, wherein the reaction is carried out at a temperature between about 380° C. to 450° C. and at a pressure between about 220 to 270 atmospheres.

23. The reaction product of claim 21, wherein the oxidant is oxygen and the amount utilized is from about 0.5 percent to about 30 percent by volume based upon the total volume of the supercritical water, the oxidant and the polymeric material.

24. The reaction product of claim 22, wherein the polymeric material is processed within a residence time of 3 minutes.

25. The reaction product of claim 24, wherein the polymeric material is PVC and the product comprises at least about 5 percent on a weight basis of vinyl chloride, and at least 10 percent on a weight basis of ethylene dichloride.

26. The reaction product of claim 24, wherein the polymeric material is a polyolefin and the reaction product is predominately methane, ethylene, propylene and acetic acid.

27. The reaction product of;
a polymer and an oxidant in the presence of supercritical water.

28. The reaction product of claim 27, wherein the polymeric material is polyvinyl chloride, polyethylene, polycarbonate, polystyrene or polyvinyl acetate.

29. The reaction product of to claim 28, wherein the reaction is carried out at a temperature between about 380° C. to 450° C. and at a pressure between about 220 to 270 atmospheres.

* * * * *